United States Patent [19]

Carlisle

[11] 4,312,635
[45] Jan. 26, 1982

[54] METHOD AND APPARATUS FOR FLUID ANALYSIS

[75] Inventor: Charles T. Carlisle, Katy, Tex.

[73] Assignee: Geochem Research, Inc., Houston, Tex.

[21] Appl. No.: 161,351

[22] Filed: Jun. 20, 1980

[51] Int. Cl.³ .................. G01N 33/18; G01N 33/22
[52] U.S. Cl. .................. 23/230 R; 23/230 HC; 422/68; 422/81
[58] Field of Search ......... 23/230 R, 230 M, 230 HC; 422/81, 82, 68; 73/425.4 R

[56] References Cited

U.S. PATENT DOCUMENTS

| | | | |
|---|---|---|---|
| 2,933,293 | 4/1960 | Ferrari, Jr. | 23/230 R X |
| 3,933,430 | 1/1976 | Hare | 23/230 R |
| 4,130,394 | 12/1978 | Negersmith | 23/230 R |
| 4,224,033 | 9/1980 | Hansen et al. | 23/230 R |

Primary Examiner—Ronald Serwin
Attorney, Agent, or Firm—Pravel, Gambrell, Hewitt, Kirk, Kimball & Dodge

[57] ABSTRACT

A fluid is circulated in a loop at a predetermined pressure and temperature. A second immiscible fluid is added to the loop and maintained in a portion of the loop so that a portion of the loop is free of the second immiscible fluid. A chemical tracer is added to the fluids and allowed to partition between them. Samples are taken of the mixture of first fluid and tracer from a portion of the loop free of the second fluid. From this sample, calculations may be made to determine the partition co-efficient of the fluids.

20 Claims, 1 Drawing Figure

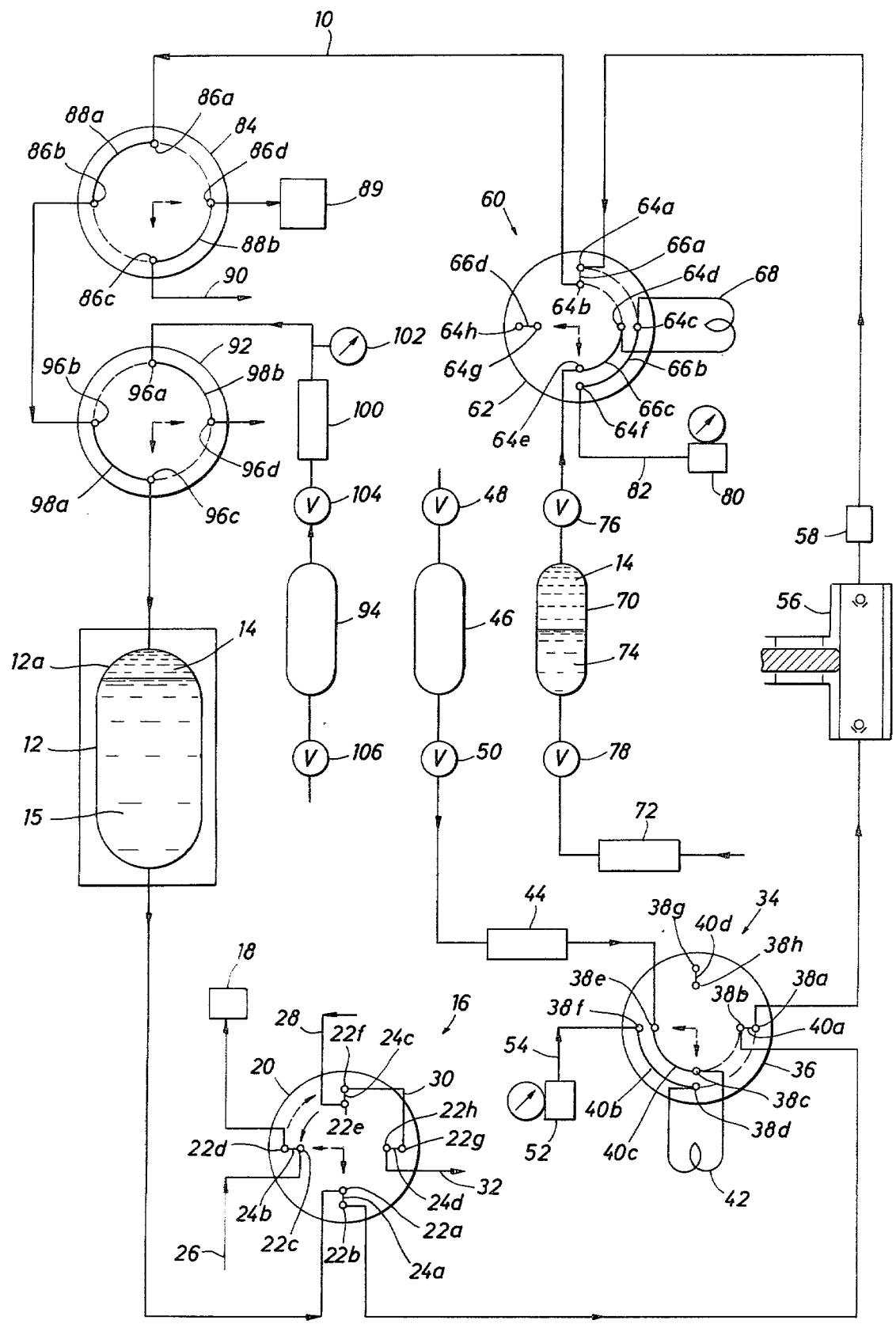

METHOD AND APPARATUS FOR FLUID ANALYSIS

TECHNICAL FIELD

This invention relates to a method and apparatus for fluid analysis when the fluid must remain at a predetermined temperature and pressure. More specifically, this invention relates to a method and apparatus for the determination of partition co-efficients which may be used in single-well tracer techniques to determine residual oil saturation.

PRIOR ART

There are many analytical operations which require fluids to be circulated at a predetermined temperature and pressure. When measured amounts of one or more fluids must be added to the circulatory fluid and samples taken for testing without changing the fluid environment, the problems faced are considerable. Fluid analysis used in certain tertiary oil recovery evaluations, for example, require such control.

In determining whether a given oil field is suitable for tertiary oil recovery, it is important to know the distribution and amount of residual oil. Such information is necessary for the selection of the method and evaluation of the economics of tertiary recovery. While there are a number of methods for estimating the residual oil saturation ($S_{or}$) in reservoirs, each one has advantages and limitations. One of the best methods, single-well tracer technique, has the advantage that it measures $S_{or}$ in a larger fraction of the reservoir farther away from the well-bore than other methods. Moreover it provides an effective or average saturation, weighted toward the oil remaining in the more permeable zones that will be most accessible to the flood brine and/or chemicals used in the recovery.

The single-well tracer technique is disclosed in U.S. Pat. No. 3,623,842, "Method of Determining Fluid Saturations in Reservoirs." This method requires the determination of partition coefficients of tracers between the carrier fluid and the oil in the reservoir. Partition coefficients are generally called K-values and are equal to the concentration of the tracer in the oil divided by the concentration of the tracer in the brine used as carrier fluid after the tracer has had time to partition between the two fluids. K-values may be determined prior to field tests in the laboratory as a function of K-value against the concentration of tracer in the carrier at equilibrium. These K-values may then be used in conjunction with field measurements to determine $S_{or}$.

Because the K-value is sensitive to temperature, pressure, brine salinity, and crude oil type, K-values can vary substantially. It is necessary to recreate the well conditions in the laboratory for each reservoir to be tested. This often includes high temperatures, high pressure situations, and it has proven difficult to determine the K-value rapidly and accurately.

One method used in determining K-values is the static equilibrium cell method. A simple equilibrium cell of known internal volume is filled with brine containing a tracer of known concentration. The cell is raised to reservoir temperature and maintained at reservoir pressure. Crude oil is then pumped into the cell through one valve while brine leaves through a second valve to be measured. After the oil volume has entered the cell, the valves are closed and the cell is rocked to achieve equilibrium. Samples are then taken to measure the equilibrium tracer concentration. The calculation of a K-value can then be made. This method has the following drawbacks:

1. Sampling of liquids containing dissolved gases at at high pressure is quite difficult. Gas evolution can cause sample size variation if hypodermic sampling is used. High pressure sampling valves are difficult to use at these conditions (up to 5000 psi) when brine is to be sampled in very small quantities (a few microliters);
2. only a single point on the K-value graph can be determined per run. The system must be broken down and cleaned between runs;
3. there is no direct indication that equilibrium has truly been reached. The system must be rocked and sampled until the tracer concentration appears to be constant. This is a problem when highly reactive esters are being used as tracers; and
4. this procedure is not continuous and is very time consuming.

A description of such a method may be found in the Appendix to "Description of Field Tests to Determine Residual Oil Saturation by Single-well Tracer Method" by Clyde Q. Sheely, Journal of Petroleum Technology, p. 194 (Feb. 1978).

A second known method is the dynamic (column flow) method. Some of the drawbacks of the static equilibrium cell method are avoided by the dynamic method where brine containing tracers is forced through a packed column at a constant rate. After a baseline concentration is established by gas chromatography sampling at the column exit, a known volume of crude oil is admitted to the column. Brine with tracer is permitted to flow again. The oil is trapped by the column packing and exposed to brine containing tracer. The output concentration may then be used to determine a K-value. The dynamic method still requires high pressure gas chromatography sampling with its inherent troubles, like the procedure described above, is not continuous and must be repeated for each K-value determined.

SUMMARY OF THE INVENTION

A method and apparatus has been developed in accordance with the invention which is used to determine K-values faster and more effectively than possible in the prior art.

A circulation loop is filled with a first fluid which is circulated at a substantially constant temperature and pressure. A measured amount of a chemical tracer is added to the fluid in the circulation loop at substantially the same temperature and pressure as the fluid in the circulation loop. The circulation fluid is sampled to determine when an equilibrium concentration value is obtained which means that the first fluid and tracer are thoroughly mixed. Then a measured amount of a second fluid, which is immiscible with the first fluid, is added into circulation loop at substantially the same temperature and pressure as a fluid in the circulation loop. The second fluid is maintained in a portion of the circulation loop, known as an equilibrium cell, which has an inlet and outlet located so that one of the immiscible fluids will collect in the cell and the other fluid as it circulates through the cell will flow through the first fluid. Samples of the mixture of the first fluid and tracer are taken from the portion of the circulation loop free of the second fluid to determine when equilibrium is again reached and the concentration value is then found. Subsequent concentration values are found by the repeated addition of tracer and sampling of mixture of first fluid and tracer.

When the invention is used to find K-values for the determination of residual oil saturation, the first fluid will be brine, the second fluid will be oil and the third fluid will be an ester or alcohol.

BRIEF DESCRIPTION OF THE DRAWINGS

FIG. 1 is schematic representation of the apparatus of the present invention.

DESCRIPTION OF A PREFERRED EMBODIMENT

For simplicity of description, the apparatus of the present invention, as shown schematically in FIG. 1, will first be described beginning with the circulation loop 10 as it connects with an equilibrium cell 12 and continue along circulation loop 10 in a counter clockwise direction which is also the direction of flow in the system. After the apparatus has been described, a preferred embodiment of the method of the present invention will be described. The circulation loop 10 is made of steel tubing with an inner diameter of 0.040 inches and suitable for use with pressures of up to 5,000 psig and temperatures of up to 250° F. The present invention may be used to simulate oil reservoir conditions so all the apparatus must be able to withstand such temperature and pressure. The circulation loop 10 is formed of a number of portions of tubing connecting the various elements of the apparatus.

The equilibrium cell 12 is formed of a larger diameter steel tube with an inner diameter of 0.375 inches. The length of the equilibrium cell may vary from approximately 4 to 12 inches. The total volume of the system varies with the length of the equilibrium cell 12 as well as the length of the component tubing of circulation loop 10. The total volume of the system must be known for calculation purposes and may be found by measuring the fluid required to fill the system. The equilibrium cell 12, as well as the other elements of the system, will be mounted in the circulation loop 10 by fittings (not shown) well known in the art which are suitable for the temperature and pressure in the system and allow only minimal or no dead volume. The equilibrium cell 12 is mounted vertically so that the lighter fluid 14 of two immiscible fluids 14 and 15 will be maintained in the upper portion 12a of the equilibrium cell 12 near its inlet opening and not flow through the entire system. The lighter fluid 15 will flow through the system and interact with the fluid 14 as it flows through the equilibrium cell 12.

The circulation loop 10 is connected to a sampling valve means 16 through which measured amounts of fluid are taken from the system and directed toward a detector 18, such as a flame ionization gas chromatograph (not shown). An eight-port sampling valve 20 of the sampling valve 16 must be, as must all of the valves of the present invention, suitable for operation at the temperature and pressure conditions of the system and must be capable of rapidly and accurately allowing small measured quantities of fluid to flow through various ports as described in detail below. VALCO sampling and switching valves (trademarked products of Valco Instruments Co. of Houston, Tex.) are suitable for these purposes. These valves include internal rotors with grooves cut in them which allow fluid communication between various ports depending on the valve position. Because the grooves are designed to hold specific volumes they may be used to transport measured amounts of fluid.

Eight sample valve ports 22a-h are connected for fluid communication in pairs by grooves 24a-d, respectively. When valve 20 is in a first position, indicated in FIG. 1 by solid lines, the ports 22a and 22b connect circulation loop 10 through the groove 24a which has a volume of two microliters. Ports 22c and 22d are connected through groove 24b to a carrier gas line 26 leading to detector 18. A fresh water line 28 used for flushing extends from the port 22e, through the groove 24c to the port 22f and through the jumper line 30 leading to port 22g, groove 24d and port 22h which connects to drain line 32.

When the valve 20 is turned 90° and moved to a second position, indicated by broken lines, groove 24a moves to ports 22c and 22d thereby inserts two microliters of fluid from circulation loop 10 into the carrier line 26 leading to detector 18 where the sample may be analyzed. At the same time, groove 24b moves between ports 22e and 22f where it is filled with fresh water. Circulation may continue uninterrupted in loop 10 as groove 24d moves between ports 22a and 22b. When valve 20 is moved back to its first position, the fresh water in groove 24c will enter the carrier line 26 and flush out any residue from the fluid from the circulation loop 10. Preferably, movement of the sampling valve, as well as the other valves in the system, is mechanically actuated.

The circulation loop 10 continues to a tracer valve means 34 which uses a similar eight-port, two-position valve 36. When the tracer valve 36 is in a first position, indicated by the solid lines, a pair of ports 38a and 38b connect the circulation loop 10 through a groove 40a to allow fluid communication. A second pair of ports 38c and 38d are connected to a tracer tube or loop portion 42. Port 38e is connected through a line to pump 44 which pumps fluid from a reservoir 46 which will hold the chemical tracer. The reservoir 46 may be filled and emptied through valves 48 and 50. Port 38f is connected to a back pressure regulator 52 which assures the fluid in line 54 being held at a set pressure. In the first position, grooves 40b and 40c connect the loop portion 42 to the pump 44 and regulator 52 so that the loop portion 42 may be filled from reservoir 46 and held at a set pressure. The loop portion 42 is formed of tubing with an 0.012 inch internal diameter and is of a length such that the loop portion 42 and grooves 40b and 40c hold 50 microliters. The fourth pair of ports 38g and 38h are not used by tracer valve means 34.

When the tracer valve 36 is moved 90° to a second position, indicated by the broken lines, the grooves 40b and 40c connect loop portion 42 to the circulation loop 10 and the 50 microliters of chemical tracer enters into the circulation loop 10. By repeated movements of valve 36, accurately measured amounts of tracer are added to the system, so the tracer concentration may be accurately increased by known amounts.

The circulation loop 10 includes a circulation pump 56 which provides positive flow of fluid in the circulation loop at a fixed rate. A pressure transducer/safety monitor 58 is inserted in the circulation loop 10 as a safety device to avoid accidental over-pressurization of the system.

The circulation loop continues to a second fluid valve means 60 which also includes an eight-port, two-position valve 62. When the tracer valve 62 is in a first position, indicated by solid lines, a pair of ports 64a and 64b connect the circulation loop through groove 66a to allow fluid communication. The pair of ports 64c and 64d are connected to a tube or loop portion 68. Port 64e is connected through a line to a reservoir 70 which contains the second fluid 14 which may be oil. It is pumped out of reservoir 70 by pump 72 acting on mercury 74 held in reservoir 70. The reservoir 70 may be filled and emptied through valves 76 and 78. Port 64f is connected to a back pressure regulator 80 which assures the fluid in line 82 being held at a set pressure. In the first position, grooves 66b and 66c connect the loop portion 68 to the pump 72 and regulator 80 so that the loop portion 68 may be filled with oil 14 from reservoir 70 and held at a set pressure. The loop portion 68 is formed of tubing with a 0.040 inch internal diameter and is of a length such that the loop portion 68 and grooves 66b and 66c hold 5 milliliters. The fourth pair of ports 64g and 64h are not used by tracer valve 60.

When the tracer valve 62 is moved 90° to the second position indicated by broken lines, grooves 66b and 66c connect loop portion 68 to the circulation loop 10 and the 5 milliliters of oil enters into the circulation loop 10. Because some oil adheres to the walls of loop portion 68 and because it is desirable that all fluids be accurately measured, the valve 62 is left in position with loop portion 68 as part of circulation loop 10 once the oil has entered the system. Thus all the oil, even that adhering to the wall, contributes to the partitioning of the chemical tracer.

The circulation loop 10 also includes a valve 84 which is a four-port, two-position valve used to empty the system. In the solid line position, ports 86a and 86b and groove 88a allow circulation in loop 10. In the second dotted line position, ports 86a and 86d with groove 88b connect the circulation loop 10 to a vacuum pump 89 which drains the system. Line 90 vents the system while draining. The vacuum pump 89 is also used to ensure a dry system prior to filling.

The circulation loop 10 includes a valve 92 which is also a four-port, two-position valve. Valve 92 is used to fill the system with brine 15 from reservoir 94. In the solid line position, ports 96a and 96b and groove 98a allow circulation in loop 10. In the second, dotted line position, ports 96a and 96d with groove 98a connect the circulation loop 10 to pump 100. Pump 100 fills the system with brine 15 from the reservoir 94. Pump 100 is capable of accurate measurement of fluid flow so that the volume of brine 15 in the system can be known. Pressure indicator 102 allows the pressure in circulation loop 10 to be set at the desired level. The reservoir 94 may be filled and emptied through valves 104 ad 106. From valve 92, the circulation loop 10 continues to equilibrium cell 12.

The fluid is kept at the desired temperature by a temperature control means (not shown) such as an oven which can contain the system. Portions of the system where partitioning of the tracer does not occur, such as sampling, the reservoirs and reservoir pumps, may if desired, be left out of the oven for convenience so long as the temperature of the fluid where partitioning does occur is not affected.

To cause better interacting of the fluids and their quicker partitioning of the tracer, the equilibrium cell 12 may be packed with steel wool.

METHOD OF OPERATION

Prior to use, all portions of the system are cleaned, then assembled and evacuated. Reservoir 94 is filled with brine of identical solution to that which will be used in field tests. Reservoir 46 is filled with the chemical tracer to be used, which preferably is an ester. Reservoir 70 is filled with the second fluid, which when K-values for single-well tracer tests are to be calculated, is oil from the reservoir to be tested. Valves 20, 36, 62 and 84 are in the first position, as indicated in FIG. 1 by solid line. The system filling valve 92 is in the second position, as indicated by broken lines. The oven or other temperature control means to control the temperature of the fluid in the circulation loop 10 is set at the temperature of the oil reservoir from which the oil 14 is taken. The system is filled with the brine 15 from reservoir 94 by pump 100 through valve 92. The pumping is continued until the circulation loop 10 is filled and the pressure indicator 102 shows that the system is at the pressure of the oil reservoir. Valve 92 is then turned to the first position to form a continuous circulation loop. Circulation pump 56 is turned on to provide a positive displacement, constant flow circulation to the system. The total volume of fluid in the system is approximately twenty-five milliliters and the flow is approximately 5.6 circulations per hour. The exact volume of brine in the system, which is needed for later calculations, is read from pump 100.

The pump 44 fills loop portion 42 with 50 microliters of the chemical tracer from reservoir 46. The back pressure regulator 52 ensures that this fluid is held in loop 42 at the same pressure as the fluid in loop 10. Tubing portion 16 is filled with 5 milliliters of oil from reservoir 70 by pump 72. The pressure of the oil in loop 68 is kept at the system pressure by back pressure regulator 80. The valve 36 is then moved to its second position whereby the 50 microliters of ester are entered into circulation loop 10.

The sampler valve 20 periodically takes two microliter samples of the brine and tracer mixture to the flame ionization gas chromatograph 18 from which the amount of tracer in the two microliters may be determined and, thereby, the concentration of the tracer in the brine is determined. This figure may also be calculated from the proportion of tracer added to the system to the volume of brine in the system. This provides a check of the accuracy of the measurements. When the same tracer concentration level has been indicated by sufficient consecutive readings, it may be assumed that the system is in equilibrium. Three consecutive sample values have been chosen to indicate equilibrium. Samples are taken at fifteen minute intervals although other intervals may be used.

The second fluid valve 62 is then turned to its second position, thereby placing loop 68 on line with circulation loop 10 and depositing the 5 milliliters of oil in the circulation loop 10. Because the fluid in loop 68, as well as the tracer in loop 42, is at the system temperature and pressure when those loop portions are added to the circulation loop, no change in the fluid temperature or pressure occurs. Because the volume of the added loop portions are known, the total system volume also may be accurately calculated. Once loop 68 is on line, it is left in position. The oil from loop 68 moves along circulation line 10 to reservoir 12. Because reservoir 12 is vertically mounted and the oil is of a lighter density than the brine, the oil remains in the upper portion 12a of the equilibrium cell 12 adjacent the inlet from the loop 10. The brine and tracer mixture continues to circulate through loop 10. As the brine flows through the oil in equilibrium cell 12, the tracer partitions between the two fluids. The tracer partitioning into the oil reduces the concentration of the tracer in the brine.

Some oil remains on the walls of the loop 68 and circulation loop 10 between valve 62 and equilibrium cell 12. As this adhering oil is also exposed to the brine and tracer mixture, partition occurs with this oil and calculations based on an oil volume of 5 milliliters are accurate.

The sampling valve 20 continues to be used to take samples of the brine and tracer mixture and to evaluate tracer concentration in the brine. A new equilibrium concentration value of tracer in brine is indicated by repeated identical values from the flame ionization gas chromatograph. This value may be used to calculate the amount of tracer which has been partitioned into the oil which is then used to determine the concentration of tracer in oil. A K-value equal to the concentration of the tracer in oil divided by the concentration of the tracer in brine may then be calculated as was desired.

The valve 36 is then changed to the first position so that another measured portion of tracer may be added into loop 42 and the valve is then returned into the loop 10 so that the tracer enters the circulation loop 10. This provides a new concentration of tracer in brine and as the brine and tracer circulate through equilibrium cell 12, the tracer partitions again between the oil and brine. The sampling valve 20 then continues to take samples to be tested for tracer and another K-value may be determined. This procedure may be continued by the adding of tracer and increasing concentration of tracer in brine until all the desired K-values have been determined.

This system may also be used for other fluids and chemical tracers when it is desired to determine the partition co-efficients of any fluids.

The foregoing disclosure and description of the invention are illustrative and explanatory thereof and various changes in the size, shape and materials as well as the details of the illustrated construction and operation may be made without departing from the spirit of the invention.

I claim:

1. Method for fluid analysis, comprising the steps of:
   (a) circulating a first fluid in a closed loop at a predetermined temperature and pressure;
   (b) adding a measured amount of a second fluid, which is immiscible in relation to the first fluid, into the loop;
   (c) maintaining the second fluid in one portion of the loop so that another portion is free of the second fluid;
   (d) adding a measured amount of a chemical tracer to the fluid in the loop; and
   (e) sampling, from the portion of the circulation loop free of the second fluid, the first fluid mixed with tracer after equilibrium is obtained to determine the concentration of tracer in the first fluid.

2. Method of claim 1, wherein:
   step (b) includes adding the second fluid at the same temperature and pressure as the first fluid.

3. Method of claim 1, wherein:
   step (d) includes adding chemical tracer at the same temperature and pressure as the first fluid.

4. Method of claim 1, wherein prior to step (b) the following steps are performed adding a measured amount of a chemical tracer to the fluid in the loop; and
sampling the first fluid mixed with tracer after equilibrium is obtained to determine the concentration of tracer in the first fluid.

5. Method of claim 1, wherein the step of sampling includes:
   removing a measured portion of the circulating fluid and tracer mixture and determining amount of tracer in said measured portion.

6. Method of claim 1, wherein:
   steps (d) and (e) are repeated.

7. The method of claim 1, wherein:
   the first fluid is brine and the second fluid is oil.

8. The method of claim 7, wherein:
   the temperature and pressure at which the fluid in the circulation loop is maintained is substantially the temperature and pressure of a reservoir from which the oil was obtained.

9. The method of claim 8, wherein the step of adding a measured amount of chemical tracer includes:
   filling a first tubing section with the measured amount of chemical tracer at substantially the same temperature and pressure as the fluid in the circulation loop;
   inserting the first tubing section containing the measured amount of chemical tracer into the circulation loop; and
   removing the first tubing section from the circulation loop after the equilibrium concentration value is obtained.

10. The method of claim 8, wherein the step of adding a measured amount of a second fluid includes:
    filling a second tubing section with the measured amount of the second fluid at substantially the same temperature and pressure as the fluid in the circulation loop;
    inserting the second tubing section containing the measured amount of oil into the circulation loop.

11. The method of claim 8, wherein the step of sampling includes:
    removing a third section from the circulation loop;
    moving the third section into a carrier gas line leading to a flame ionization gas chromatograph; and
    returning the third section into the circulation loop.

12. The method of claim 11, wherein the step of sampling further includes:
    flushing the carrier gas line.

13. The method of claim 8, wherein the step of maintaining a portion of the circulation loop free of the second immiscible fluid includes:
    retaining substantially all of the second fluid in an equilibrium cell.

14. The method of claim 1, wherein:
    the chemical tracer is an ester.

15. The method of claim 1, wherein:
    the chemical tracer is an alcohol.

16. Apparatus for the analysis for fluid comprising:
    a circulation loop;
    circulation means for circulating fluid in the loop;
    temperature control means for maintaining fluid in said circulation loop at a predetermined temperature;
    pressure control means for maintaining fluid in said loop at a predetermined pressure;
    an equilibrium cell in fluid communication with said circulation loop suitable for containing two immiscible fluids, the cell containing a loop inlet and outlet located so that one of the immiscible fluids will collect in the cell and the other fluid, as it circulates through the cell, will flow through said fluid;

first valve means in fluid communication with said circulation loop for selectively adding a measured amount of a chemical tracer into said circulation loop;

second fluid valve means in fluid communication with said circulation loop for selectively adding a measured amount of a second fluid into said circulation loop which is immiscible with a first fluid circulating in the loop; and sampling means in fluid communication with said circulation loop suitable for selectively removing measured quantities to be tested of the first fluid mixed with the chemical tracer from said circulation loop.

17. Apparatus of claim 16, wherein said first valve means includes:

a valve housing having first, second and third pairs of ports;

a tracer reservoir in fluid communication with said first pair of ports;

a first loop portion in fluid communicaton with said second pair or ports;

said circulation loop in fluid communication with said third pair of ports;

a valve element in the housing having first and second positions;

said first loop portion is in fluid communication with said tracer reservoir when said valve element is in said first position; and said first loop portion is in fluid communication with said circulation loop when said valve element is in said second position.

18. Apparatus of claim 16, wherein said second valve means includes:

a second fluid valve housing with first, second and third pairs of ports;

a second fluid reservoir in fluid communication with said first pair of ports;

a second loop portion in fluid communication with said second pair of ports;

said circulation loop in fluid communication with said third pair of ports;

a second fluid valve element in the housing having first and second positions;

said second loop portion in fluid communication with said second fluid reservoir when said second fluid valve element is in said first position; and said second loop portion is in fluid communication with said circulation loop when said second fluid valve element is in said second position.

19. Apparatus of claim 16, wherein said sampling means comprises:

a sampling valve housing with first, second and third pairs of ports;

a carrier gas line in fluid communication with said first pair of ports;

a flushing fluid line in fluid communication with said second pair of ports;

said circulation loop in fluid communication with said third pair of ports;

a sampling valve element in the housing having first and second positions;

said sampling valve element moving an amount of fluid from said third pair of ports to said first pair of ports when said sampling valve element is moved from said first position to said second position; and said sampling valve element moving an amount of flushing fluid from said second pair of ports to said first pair of ports when said sampling valve element is moved from said second position to said first position.

20. Apparatus of claim 16, wherein:

said portion of said equilibrium cell where the second fluid collects is packed with steel wool.

* * * * *

UNITED STATES PATENT AND TRADEMARK OFFICE
CERTIFICATE OF CORRECTION

PATENT NO. : 4,312,635
DATED : January 26, 1982
INVENTOR(S) : Charles T. Carlisle It is certified that error appears in the above-identified patent and that said Letters Patent are hereby corrected as shown below:

Column 1, line 40, please delete "coefficients" and insert therefor -- co-efficients --.

Column 1, line 42, please delete "coefficients" and insert therefor -- co-efficients --.

Column 2, line 4, please delete "at".

Column 2, line 59, please insert after "into" -- the --.

Column 5, line 54, please delete "ad" and insert therefor -- and --.

Column 8, line 58, please delete "for", second occurrence, and insert thereof -- of Column 9, line 28, please delete "or" and insert therefor -- of --.

Signed and Sealed this

Sixth Day of July 1982

[SEAL]

Attest:

GERALD J. MOSSINGHOFF

Attesting Officer

Commissioner of Patents and Trademarks